United States Patent [19]

Brannen et al.

[11] 4,215,067

[45] Jul. 29, 1980

[54] PROCESS FOR THE PREPARATION OF ZINC SALTS OF DIHYDROCARBYLDITHIOPHOSPHORIC ACIDS

[75] Inventors: Cecil G. Brannen, West Chicago; Nicolas C. Petrellis, Lisle, both of Ill.

[73] Assignee: Standard Oil Company (Indiana), Chicago, Ill.

[21] Appl. No.: 974,327

[22] Filed: Dec. 29, 1978

[51] Int. Cl.$^2$ .............................................. C07F 3/06
[52] U.S. Cl. .................................................. 260/429.9
[58] Field of Search ...................................... 260/429.9

[56] References Cited

U.S. PATENT DOCUMENTS

| | | | |
|---|---|---|---|
| 2,837,549 | 6/1958 | Reeves et al. | 260/429.9 |
| 3,086,939 | 4/1963 | Tichelaar et al. | 260/429.9 X |
| 3,168,497 | 2/1965 | Twitchett | 260/429.9 X |
| 3,290,347 | 12/1966 | Miller | 260/429.9 |
| 3,361,668 | 1/1968 | Wiese | 260/429.9 X |
| 3,471,540 | 10/1969 | Walters | 260/429.9 |

*Primary Examiner*—Helen M. S. Sneed
*Attorney, Agent, or Firm*—Mark DiPietro; William T. McClain; William H. Magidson

[57] ABSTRACT

Processes for the manufacture of substantially haze free zinc salts of dihydrocarbyldithiophosphoric acid comprising the addition of an effective amount of a surface active agent or surfactant at or prior to the neutralization of a dihydrocarbyldithiophosphoric acid by zinc oxide that reduces the Electrophoretic mobility (EM) of an untreated colloidal zinc oxide particle by about 25%. Generally the mobility of the treated colloidal zinc compound particle is reduced to less than about $1.0 \times 10^{-3}$ microns/sec. per volt/cm.

12 Claims, No Drawings

PROCESS FOR THE PREPARATION OF ZINC SALTS OF DIHYDROCARBYLDITHIOPHOSPHORIC ACIDS

This invention relates to improving manufacturing processes for the preparation of zinc salts of dihydrocarbyldithiophosphoric acids. More particularly this invention relates to preventing the formation of haze in the zinc dihydrocarbyldithiophosphate product.

Zinc dihydrocarbyldithiophosphates and similar salts are useful in automotive oils, industrial oils, hypoid gear oils, and automatic transmission fluids, primarily to impart oxidation resistance, extreme pressure properties, corrosion resistance, and detergency to the oil.

The manufacture of satisfactorily clear, odorless, and stable zinc salts of dihydrocarbyldithiophorphic acids has been found to be difficult in the past and sensitive to a variety of processing conditions. While many process improvements have been made, the products of current processes tend to be hazy. The haze does not appear to harm engines or processing equipment. Since the haze in the product can be masked by blending, the hazy zinc product can be blended into finished oils or multi-additive packages. However, the hazy zinc dihydrocaryl dithiophosphate product cannot be sold in a concentrate or single additive package.

We believe the haze results from the presence of particles of zinc oxide. The zinc oxide particles range in size from colloidal to about 500 millimicrons (millimicron) and larger. Filtration or centrifuge techniques which are common in the art are sucessful in removing the haze resulting from particles about 100-500 millimicrons in size and greater. However haze resulting from particles less than 100 millimicrons and particularly colloidal particles about 0.1 to 10.0 millimicrons cannot be removed in this way. Due to variability in process conditions small amounts of certain by products are formed which apparently interact with zinc oxide and stabilize the colloidal zinc oxide haze.

The haze can arise during the production of zinc dihydrocarbyldithiophosphate from zinc oxide particles of all sizes. The haze can be reduced by using large particles of zinc oxide. The use of small particles of zinc oxide has the advantage that more rapid reactions occur.

U.S. Pat. No. 3,562,306 teaches the use of zinc nitrate, zinc chloride, zinc sulfate and the like to promote the reaction between zinc oxide and the dihydrocarbyl dithiophosphoric acid. U.S. Pat. No. 3,290,347 teaches the use of water soluble fatty acids and water soluble metal salts of fatty acids to accelerate the reaction between the metal compound and the dithiophosphoric acid. The processes found in these patents suffer the disadvantage that while the zinc compounds and the fatty acids or salts accelerate the reaction between the zinc compounds and dihydrocarbyl dithiophosphoric acid, the colloidal zinc compound particle haze can form in the presence of these compounds. These compounds are not surface active agents and fail to substantially prevent or minimize haze formation.

Accordingly, a need exists for producing substantially haze-free zinc dihydrocarbyl dithiophosphate from large or small particle size zinc oxide.

The general object of the invention is to produce substantially haze free zinc dihydrocarbyl dithiophosphate. A further object of the invention is to substantially prevent or minimize formation of finely divided colloidal zinc oxide particles in the zinc dihydrocarbyldithiophosphate. Still another object of the invention is to prevent or minimize formation of stabilized colloidal zinc compound moieties in the zinc dihydrocarbyl dithiophosphate composition when made from small and large particles of zinc oxides. Other objects appear hereinafter.

Zeta potential is a potential arising across the interface of all solid-liquid suspensions. Specifically, the potential arises across a diffuse layer of ions surrounding a charged colloidal particle and is largely responsible for colloidal stability. Discharge or removal of some or all of the Zeta potential is accompanied by the agglomeration and precipitation of the colloidal particles.

The zeta potential of colloidal zinc oxide haze can be measured by determining the Electrophoretic Mobility (EM) of the colloidal zinc oxide in a sample of zinc dihydrocarbyl dithiophosphate containing haze. The sample is tested untreated and treated with an amount of surface agent to determine the effect of the surface agent. An effective agent will reduce or eliminate the zeta potential and the Electrophoretic Mobility. Since the Zeta potential creates a charge on the colloidal particle, the particle will move when placed in an electric field. The Zeta potential and the Zeta-meter are well known for measuring the effect of surface agents. An amount of sample to be measured is placed in a sample cell. Each end of the cell is connected to a voltage source having sufficient voltage (greater than 1,000 volts) to cause the particles to move appreciably. The particles are observed through a microscope and the movement of the particles per unit time is measured. The Electrophoretic mobility (EM) is defined as:

$$\mu/\text{sec. per volt/cm.}$$

where $\mu$=microns traveled by the particles, sec=time of travel in seconds, volts=applied voltage and cm=length of sample cell.

We have found that haze formation during the reaction of large or small particles of zinc oxide and dihydrocarbyl dithiophosphoric acid can be prevented or minimized by the addition of certain surface active agents which reduce the Zeta potential or Electrophoretic mobility by at least 25%, preferably by at least 50% to obtain maximum haze protection. Alternatively the Electrophoretic mobility is reduced to at least less than $1.0 \times 10^{-3}$ preferably less than $0.80 \times 10^{-3}$ $\mu$/sec. per volt/cm.

Briefly, the zinc dihydrocarbyl dithiophosphate compounds of this invention are made by reacting a slurry of phosphorus pentasulfide in an inert hydrocarbon diluent with an appropriate hydrocarbyl monohydroxy compound or mixture of compounds to form a dihydrocarbyl dithiophosphoric acid. The dihydrocarbyl dithiophosphoric acid is then neutralized with zinc oxide. Water of reaction is removed and the mixture is filtered to remove excess solids. In the process of this invention a surface active agent is added to the reaction mixture at or before the neutralization of the dihydrocarbyl dithiophosphoric acid with the zinc compound to prevent or minimize haze formation.

Surface active agents or surfactants useful to substantially prevent or destory haze in zinc dihydrocarbyldithiophosphates derive their activity from the presence of both hydrophilic and lipophilic functional groups. Surfactants have certain characteristic properties derived from the functional groups. Surfactants are soluble in at least one phase of a liquid system containing at least two phase such as a water-oil system. The surfactant molecules contain at least one group or radical tending to be soluble in aqueous media and at least one other group or radical tending to be soluble in non-aqueous media. Surfactant molecules or ions tend to form oriented monolayers at the interface between the two phases such as the interface between a water and an oil phase. Surfactants appear to have greater concentrations of surfactant at phase interfaces than in the bulk of the solution. Surfactants form aggregates of molecules or ions called micells when the concentration of the solute and the bulk of the solution exceeds a limiting value that is a fundamental characteristic of each solute-solvent system. Finally, solutions of surfactants exhibit a variety of functional properties such as detergency, foaming, wetting, emulsifying, solubilizing, dispersing, etc.

Surfactants useful in this invention include anionics, nonionics, cationics, and amphoterics. Examples of anionic solubilizing groups or moieties are carboxylates, sulfonates, sulfates, and phosphates. Nonionic surface active agents are solubilized by hydroxyl groups and polyoxyalkylene chains. Primary, secondary, and tertiary amines and quaternary ammonium groups are the common cationic solubilizing groups. Amphoteric surfactants are solubilized by some combination of cationic and anionic moieties. Amphoteric substances are substances which display both cationic and anionic properties depending on pH and other compounds in solution. Nonionic solubilizing groups may also be part of amphoteric, anionic, and cationic molecules. In addition to the primary solubilizing groups, other structural units contribute to the hydrophilic tendencies of surfactants such as ester linkages and amide linkages. The hydrophobic or lipophilic moities are almost invariably hydrocarbon or halogen substituted hydrocarbon groups. Practical commercial surfactants are universally mixtures of a variety of chemical compounds. Often surfactant products are polydisperse, i.e. containing molecules which are the same type but vary in chain length, molecular weight, or other structural detail.

The hydrophilic portion of an anionic surfactant is a polar group that is negatively charged often being an acidic group in aqueous solutions or dispersions. In commercial products the negatively charged polar group is commonly a carboxylate, sulfonate, sulfate, or phosphate group. Often the anionic surfactants are present either as a free acid or in a combined form such as a part of potassium, sodium, calcium, barium, magnesium, ammonium, an amine ion, etc.

Anionic surfactants useful for haze reduction can be made from carboxylic compounds such as carboxylic acids, for example, acetic, butyric, isobutyric, propionic, and valeric, isovaleric, palimitic, stearic, oleic, isostearic, sarcosinic (N-methyl-glycene), betainic (N-N dimethyl aminoacetic acid) lauric, Tall oil acids, salicylic cocoa acids, succinic acid, oxalic acid, benzoic, substituted benzoic acid, etc. Examples of sulfonate type surfactants are alkylbenzene sulfonate, such as nonyl benzene sulfonate, toluene sulfonate, xylene sulfonate, polybutene substituted benzene sulfonate, petroleum sulfonate, sulfosuccinate, sodium dioctylsulfosuccinate, potassium dinonyl sulfosucciniate, naphthalene sulfonate, N-octyl-N-alkyltaurate, amine and amide sulfonates such as stearyl diethanol amide sulfonate, lauramine sulfonate etc. beta-sulfo esters of fatty acids, alpha-olefin sulfonates, etc.

Examples of sulfates which are most commonly the reaction product of sulfuric acid and hydrocarbyl alcohols are methyl sulfate, isobutyl sulfate, tertiary amyl sulfate, octyl sulfate, lauryl sulfate, 2-ethylhexyl sulfate, cetyl sulfate, oleyl sulfate, tall oil sulfate, etc.

Examples of compounds producing phosphate type surfactants are alkyl orthophosphates such as ethylphosphate, 2-ethylhexylphosphate, octylphosphate, decylphosphate, dodecylphosphate, phenolphosphate, ethoxylated phenol phosphate, ethoxylated nonyl phenol phosphate, lecithin and derivatives, etc.

These anionic compounds can be reacted with solubilizing compounds such as polyethoxy ethanol etc. The above compounds can be used as is or in combination with a variety of substances producing salts of the acids. Examples of salt forming cations are sodium, potassium, calcium, magnesium, and amines such as methylamine, ethanolamine, tall oil amine, oleylamine, linoeylamine, dimethylamine, diethanolamine, dioleylamine, etc.

Cationic surfactants useful for haze reduction are components containing at least one hydrophilic group or radical which are amino or quaternary nitrogen containing groups. The amino or quaternary nitrogen groups bear positive charges in aqueous media. The hydrophilic nature of one amino nitrogen is generally strong enough to solubilize a lipophilic group in the surfactant in dilute solution. To increase water solubility initial primary, secondary tertiary amino groups can be introduced or the amino group can be quaternized with low molecular weight alkyl groups such as methyl, ethyl, isopropyl, hydroxyethyl, etc. These surfactants can also be reacted with other surfactant producing compounds such as polyoxyethylene, etc. Specific examples of cationic surfactants include amines such as aliphatic, mono, di, and polyamines, such as methylamine, ethylamine, propylamine, isopropylamine, tertiarybutylamine, etc. Oxygen containing amines such as amine oxides, for example, cetylamine oxide, laurylamine oxide, cetyl amine oxide, hydrogenated fatty acid amine oxide, etc. Amine oxides can also be produced with ethanol amine substituents in place of the alkyl substituent. For example, diethanol cetylamine oxide. Further examples of cationic amine compounds are polyoxyethylene aliphatic amines, polyoxyethylene amine oxides, polyoxyethylene fatty alkyl 1,3-propene diamine, etc. Examples of effective quaternary ammonium salts are tetrametylammonium chloride, tetrastearylammonium chloride, trimethylstearylammonium chloride, trimethylcetylammonium chloride, triethylstearylammonium chloride, dimethylstearylbenzylammonium chloride, benzyl trialkylammonium chloride, triethanol stearyl ammonium chloride, etc.

Nonionic surfactants useful for haze reduction bear essentially no charge when dissolved in aqueous media. The hydrophilic nature of nonionic surfactants is derived from oxygen-containing moieties in the molecule which hydrate in water solution through hydrogen bonding. Hydrophilic tendencies are derived from ether linkages, hydroxyl groups, and to somewhat lesser extent, ester and amide linkages. One form of nonionic surfactant is a polyoxyalkylene surfactant, for example, polyoxyethylene. The solubility of these products results from the presence of the oxygen in the ether linkages between ethylene units. Polyoxyethylenes are produced by the polymerization of ethylene oxide. Polyoxyalkylene groups can be used to derivatize a variety of substances producing valuable surfactants. For instance, alkoxylated alkylphenols, alkoxylated aliphatic alcohols, carboxylic esters of polyoxyalkylene groups, polyoxyalkylated carboxylic amides, and other nonionic functions. Polyalkoxy substituted phenols are very widely used nonionic surfactants. The phenols can be substituted with other substantially hydrocarbyl groups such as methyl, ethyl, propyl, isopropyl, butyl, tertiary butyl, nonyl, dodecyl, octyl, etc. These surfactants are produced by the reaction of a substituted or nonsubstituted phenate ion with ethylene oxide promoting the further polymerization of the ethylene oxide.

Specific examples of nonionic surfactants are nonyl alkylphenoxy poly(ethoxy) ethanol, phenoxy poly(ethoxy) ethanol and formaldehyde resins, dinonyl phenoxy polyoxyethylene ethanol, oleyl polyoxyethylene ethanol, stearyl polyoxyethylene ethanol, cetyl polyoxyethylene ethanol, glycerol esters of fatty acids such as mono stearyl glycerate, monolauryl glycerate, monoricinoyl glycerate, distearyl glycerate, oleyl stearyl glycerate, tolyl glycerate, etc. Polyethylene glycol esters of carboxylic acids such as oleyl polyethylene glycerate, stearyl polyethylene glycol glycerate, etc., polyoxyethylene, sorbitan monolaurate, polyoxyethylene sorbitan trioleate, polyoxyethylene sorbitan distearate, ethoxylated castor oil, cocoa diethanol amide, lauryl diethanol amide, myristyl diethanol amide, stearyl monoethanol amide, etc.

A variety of derivatives of carboxylic acid esters such as glycerol esters, polyethylene glycol esters, sorbitol and anhydro sorbitol esters ethoxylated and phenol esters, ethylene and diethylene glycol esters, natural fats and oils, and ethoxylated fats and oils and other carboxylic acid esters are useful surfactants. One useful type of an ionic surfactant is sorbitan esters such as sorbitan monooleate, monostearate, monolaurate, etc.

Carboxylic amides are another type of nonionic surfactants. Carboxylic acids are reacted with amines such as diethanol amine, ethanol amine, isopropanol amine, methyl amine, dimethylamine, ethyl amine.

Polyalkoxy substitued phenols are very widely used nonionic surfactants. The phenols can be substituted with other substantially hydrocarbyl groups such as methyl, ethyl, propyl, isopropyl, butyl, tertiary butyl, nonyl, dodecyl, octyl, etc. These surfactants are produced by the reaction of a substituted or nonsubstituted phenate ion with ethylene oxide promoting the further polymerization of the ethylene oxide.

A variety of derivatives of carboxylic acid esters such as glycerol esters, polyethylene glycol esters, sorbitol and anhydrosorbitol esters, ethoxylated and phenol esters, ethylene and diethylene glycol esters, natural fats and oils and ethoxylated fats and oils and other carboxylic acid esters. One useful type of an ionic surfactant is sorbitan esters such as sorbitan monooleate, monostearate, monolaurate, etc.

Carboxylic amides are another type of nonionic surfactants. Carboxylic acids are reacted with amines such as diethanol amine, ethanol amine, isopropanol amine, and other amines.

Substances which contain both acidic and basic hydrophilic moieties are considered amphoteric substances. Examples of these substances are amino acids, carboxymethyl ammonium hydroxides, imidazolines containing carboxylic groups, etc.

Substances which contain both acidic and basic hydrophilic moieties are considered amphoteric substances. Examples of these substances are amino acids, carboxymethyl ammonium hydroxides, etc. Preferred surfactants for reasons of ability to substantially prevent or minimize haze formation with minimal concentration of surfactant are alkyl polyols, alkyl polyesters, polyethylene oxide, sorbitan monocarboxylate, alkyl phenoxy polyethoxy ethanol, dialkyl sodium sulfosuccinate, and formaldehyde/alkyl phenoxy polyethoxyethanol resins.

The important characteristic of the surface active agent is the ability to substantially prevent or destroy colloidal haze. Generally we have found that surface active agents which reduce Zeta potential electrophoretic mobility by 25% preferably by 50% or reduce the electrophoretic mobility to less than $1.0 \times 10^{-3}$ or preferably less than $0.80 \times 10^{-3}$ $\mu$/sec. per volt/cm. effectively prevent or destroy colloidal haze. The surfactants selected in this manner are then used in the production of the zinc dihydrocarbyl dithiophosphate at a concentration sufficient to prevent or minimizing haze formation.

The surface active agents can be used in concentrations in the reaction mixture from about 1 to about 3,000 parts per million. The concentration used in any specific application depends on the nature of the surfactant and the amount of zinc oxide colloidal particles present in the mixture. Preferably the concentration of the surfactant is maintained at as low a level as possible to avoid waste of the surfactant. In most applications, the surfactant will be effective to remove haze at a concentration from about 50 to about 2,500 parts per million based on the total reaction mixture.

Substantially hydrocarbyl monohydroxy compounds useful in the production of dihydrocarbyl dithiophosphoric acids comprise both aliphatic and aromatic monohydroxy compounds. The useful monohydroxy compounds contain from about 1 to 100 carbon atoms. Example of useful hydrocarbyl monohydroxy compounds are methanol, ethanol, proponol, isopropanol, butanol, isobutanol, tertiary butanol, pentanol, hexanol, cyclohexanol, methyl cyclohexanol, decanol, eicosanol, pentacosanol, triacontanol, pentacontanol, and hectanol, etc. Examples of useful aromatic hydrocarbyl monohydroxy compounds are phenol, naphthol, hydroxy anthracene, substituted phenols such as 4-methyl phenol, dodecyl phenol, nonylphenol, etc. Phenols substituted with alkyl groups derived from the alkylation of phenol with olefinic polymers derived from $C_3$ or $C_4$ olefinic monomers can also be used. Examples of these phenols are polybutyl phenol or polypropyl phenols having molecular weights from about 300 to 1,000.

Preferably a mixture of hydrocarbyl monohydroxy compounds are used such as mixture of isobutyl, isoamyl and isooctyl alcohols. Mixtures of both aliphatic and aromatic monohydroxy compounds can also be used for the increased stability.

Phosphorus pentasulfide is useful in the process of this invention but other phosphorus sulfides such as $P_4S_7$, $P_5S_9$, etc., can be used with somewhat less successful results.

Zinc zinc oxide is used in the production of the zinc salts of the invention for reasons of low cost, reactivity, availability, and that water, the neutralization by-product, is easily removed in processing.

In somewhat greater detail phosphorus pentasulfide is slurried in an inert hydrocarbon solvent. Solvents useful in this invention are both aliphatic and aromatic solvents inert to the presence of metal compounds, phosphorus pentasulfide, and alcohols as taught herein. Examples of useful inert solvents are hexane, heptane, benzene, xylene, toluene, $C_9+$ aromatic stream, lingroin, petroleum ethers, and petroleum distillate fractions. Preferably lubricating oils are used to control viscosity and to provide ease of blending in finished lubricating oil concentrates, packages, and products. Preferably 5W oil is used for reasons of the low viscosity.

The phosphorus pentasulfide slurry is reacted with about 4 moles (3 to 5 moles) of an alcohol or mixtures of alcohols as discussed above preferably an amount of $P_2S_5$ is added that little $P_2S_5$ remains after reaction. To avoid decomposition, the reaction is performed at temperatures from about 30° to 250° C. under an inert atmosphere. Preferably the reaction is conducted at a temperature of about 100° C. for about 3 to 4 hours. The end of the reaction is reached when the specific gravity attains a constant level. The reaction product is then stripped and cooled with an inert gas such as nitrogen to remove all traces of hydrogen sulfide, and other volatile material. Unreacted $P_2S_5$ or other solids can be removed at this step or by filtration.

Zinc oxide is then contacted with the dihydrocarbyl dithiophosphoric acid in approximately stoichiometric amounts. The reaction is performed at a temperature between about 30° and about 250° C., preferably less than about 100° C. to prevent the decomposition of the organic constituents. The zinc oxide is added to the dihydrocarbyl dithiophosphoric acid at a rate that the temperature of the reaction does not exceed about 100° C. The reaction is continued for a period of time to insure completion. Water is then removed by stripping the reaction mixture with a nitrogen stream. The product can be filtered or centrifuged in well known procedures to remove residual solids.

The surfactant can be added to the reaction mixture at any stage up to and including the reaction of the zinc oxide with the dihydrocarbyl dithiophosphoric acid. Preferably to reduce decomposition of surfactant the surfactant is added just prior to the reaction of the zinc oxide and the dithiophosphoric acid. The surfactant and the zinc oxide can be slurried in oil and then added to the dihydrocarbyl dithiophosphoric acid. The surfactant can also be added directly to the dihydrocarbyl dithiophosphoric acid. The surfactant can be dissolved in a suitable hydrocarbon diluent such as naphtha, 5W oil, hexane, etc. to aid in dissolution of the surfactant in the reaction mixture.

EXAMPLE I

To a two liter flask equipped with a nitrogen atmosphere, stirring mechanism, reflux condenser and distillation head was charged 399 grams (2 moles) of phosphorus pentasulfide and 160 grams or 200 milliliters of 5W oil. To the phosphorus pentasulfide-oil slurry was added 590 grams (8 moles) of a mixed alcohol containing 65 mole percent isobutanol, 25 mole per cent mixed amyl alcohols, and 10 mole percent octanol. The mixture was heated and stirred at a temperature of 100° C. (220° F.) for an hour. The mixture was stripped of volatiles with nitrogen stream at 100° C. (220° F.) for 15 minutes. The mixture was then cooled to 65° C. (150° F.) and filtered. To a slurry of 26 grams of AZO-77S small particle size (0.8–1.3 millimicron) zinc oxide in 50 grams of 5W oil was added 170 grams of the dihydrocarbyldithiophosphoric acid made above. The acid was added to the zinc oxide over a 10 minute period at a rate such that the temperature was maintained between 85° to 95° C. (180° to 200° F.) Water was removed by stripping with nitrogen at about 1 milliliter of nitrogen per minute at 210° F. for 40 minutes. The mixture was then filtered through 10 grams of cellite filter aid on filter paper using no vacuum. The product was opaque and white from the presence of colloidal zinc.

EXAMPLE II

Example I was repeated except that 0.50 grams of a mixture of a polyethylene oxide ethylene glycol ether and formaldehyde/octyl polyoxyethylene phenol resin was added prior to the reaction of the dihydrocarbyldithiophosphoric acid with the zinc oxide. The product was clear and bright.

EXAMPLE III

Example II was repeated with the surfactants listed in Table I.

TABLE I

ELECTROPHORETIC MOBILITY (EM) OF ZINC OXIDE PARTICLES @ 7000 ± 500v IN ZETA POTENTIAL TEST

| SURFACTANT | CONC (ppm) | Mricrons/sec. per volt/cm. | APPEARANCES |
|---|---|---|---|
| NONE | — | $1.2 \times 10^{-3}$ | Opaque - white |
| Mixture of ethylene glycol ether of polyethoxy ethanol and formaldehyde/octyl phenoxy polyethoxy ethanol resin | 500 | $0.87 \times 10^{-3}$ | clear (no haze) |
| oxide | 2500 | — | clear (no haze) |
| Octylphenoxy poly (ethylene oxy) ethanol | 2500 | — | clear (no haze) |
| Mixture of 80 parts of Sorbitan monooleate, and 20 parts of polyethylene oxide | 2500 | — | clear (no haze) |
| Dioctyl sodium sulfosuccinate | 2500 | — | clear (no haze) |

An examination of Table I shows that the haze was completely removed by a surface active agent that reduced the EM from $1.2 \times 10^{-3}$ $\mu$/ sec. per volt/cm. to $0.87 \times 10^{-3}$ $\mu$/sec. per volt/cm. and that certain other ionic and nonionic agents can reduce or prevent haze.

Since the examples and disclosures above are illustrative and explanatory and since many embodiments of the invention apart from the embodiments found above can be made, the invention resides in the claims appended hereafter.

We claim:

1. A process for the production of substantially haze-free zinc dihydrocarbyl dithiophosphate comprising reacting a dihydrocarbyl dithiophosphoric acid and zinc oxide in the presence of a surface active agent.

2. The process of claim 1 wherein the surface active agent is added prior to the reaction of the dihydrocarbyl dithiophosphoric acid with the zinc oxide.

3. The process of claim 1 wherein the surface active agent comprises formaldehyde/octyl phenoxy poly(e- thoxy) ethanol resin and an ethylene glycol ester of polyethoxy ethanol.

4. The process of claim 1 wherein the surface active agent is used at a concentration reducing the Electrophoretic mobility of the zinc compound particle by 25%.

5. The process of claim 1 wherein the surface active agent is used at a concentration reducing the Electrophoretic mobility to less than $1.0 \times 10^{-3}$ microns/sec. per volt/cm.

6. The process of claim 1 wherein the surface active agent is used at a concentration of about 1 to 3000 parts of surface active agent per million parts of reaction mixture.

7. The process of claim 1 wherein the surface active agent is used at a concentration of about 50 to 2500 parts of surface active agent per million parts of reaction mixture.

8. The process of claim 1 wherein the surface active agent is non-ionic.

9. The process of claim 1 wherein the surface active agent is anionic.

10. The process of claim 1 wherein the surface active agent is cationic.

11. A process for the production of substantially haze-free zinc dihydrocarbyl dithiophosphate which comprises reacting a dihydrocarbyl dithiophosphoric acid with an approximately stoichiometric amount of zinc oxide in the presence of about 50–2,500 parts of a surface active agent per million parts of the reaction mixture at a temperature of about 30°–250° C., stripping water of neutralization, and recovering the zinc dihydrocarbyl dithiophosphate.

12. The process of claims 1 and 11 wherein the surface active agent is selected from the group consisting of an alkyl phenoxy poly(ethoxy) ethanol and dialkyl sodium sulfosuccinate.

* * * * *